(12) United States Patent
Lam et al.

(10) Patent No.: US 12,083,237 B2
(45) Date of Patent: Sep. 10, 2024

(54) DEVICE AND METHOD FOR HERBS DISINFECTION

(71) Applicant: NOVAGREEN TECHNOLOGIES LTD., D.N. Hevel Megiddo (IL)

(72) Inventors: Amnon Lam, Givat Oz (IL); Eliezer Fuchs, Megiddo (IL)

(73) Assignee: NOVAGREEN TECHNOLOGIES LTD., D.N. Hevel Megiddo (IL)

( * ) Notice: Subject to any disclaimer, the term of this patent is extended or adjusted under 35 U.S.C. 154(b) by 904 days.

(21) Appl. No.: 17/053,918

(22) PCT Filed: May 8, 2019

(86) PCT No.: PCT/IL2019/050525
§ 371 (c)(1),
(2) Date: Nov. 9, 2020

(87) PCT Pub. No.: WO2019/215741
PCT Pub. Date: Nov. 14, 2019

(65) Prior Publication Data
US 2021/0220500 A1    Jul. 22, 2021

Related U.S. Application Data

(60) Provisional application No. 62/690,965, filed on Jun. 28, 2018.

(30) Foreign Application Priority Data

May 10, 2018 (IL) .......................................... 259283

(51) Int. Cl.
*A61L 2/14* (2006.01)
*H01J 37/32* (2006.01)
*H05H 1/46* (2006.01)

(52) U.S. Cl.
CPC ................. *A61L 2/14* (2013.01); *H01J 37/32* (2013.01); *H05H 1/466* (2021.05);
(Continued)

(58) Field of Classification Search
CPC .. A61L 2/14; A61L 2202/11; A61L 2202/122; A61L 2202/16; A61L 2202/14;
(Continued)

(56) References Cited

U.S. PATENT DOCUMENTS 8,771,595 B2    7/2014  Paskalov
2003/0006019 A1*  1/2003  Johnson ................... H05H 1/46
                                                    164/1
(Continued)

OTHER PUBLICATIONS

Betts (2014) Microbial update—herbs & spices. International Food Hygiene 25(1); pp. 9 and 11.
(Continued)

*Primary Examiner* — Sean E Conley
*Assistant Examiner* — Brendan A Hensel
(74) *Attorney, Agent, or Firm* — Dorsey & Whitney LLP

(57) ABSTRACT

Device and method suitable for disinfecting herbs in small quantities, e.g. for home use, using plasma, are disclosed. The device comprises a sealable vessel dimensioned and configured to contain herbs in chunks, in granular form such as particles or in powder, in a treatment region of the sealable vessel. The device further comprises a power source configured to generate electromagnetic (EM) power sufficient for plasma generation in a plasma generation region of the sealable vessel. The sealable vessel is optionally detachable from the device. A portable sealable vessel configured to store and transport herbs, the herbs being microbially sealed therein, is also disclosed. The portable sealable vessel may be positioned in a slot of the device so as to generate plasma in the portable sealable vessel and disinfect the herbs. A multi-slot device is also disclosed, enabling plasma
(Continued)

disinfection of herbs in a multitude of distinct sealable vessels.

8 Claims, 6 Drawing Sheets

(52) U.S. Cl.
CPC ...... *A61L 2202/11* (2013.01); *A61L 2202/122* (2013.01); *A61L 2202/16* (2013.01)
(58) Field of Classification Search
CPC ........... H01J 37/32; H05H 1/466; H05H 1/46; A23B 7/015; A23L 3/26
See application file for complete search history.

(56) References Cited

U.S. PATENT DOCUMENTS

| | | | |
|---|---|---|---|
| 2006/0257280 A1 | 11/2006 | Hammerstrom et al. | |
| 2012/0145041 A1* | 6/2012 | Walters .................. | B82Y 40/00 977/773 |
| 2014/0023554 A1 | 1/2014 | Paskalov | |
| 2015/0209462 A1 | 7/2015 | Turbett et al. | |
| 2017/0036184 A1* | 2/2017 | Bormashenko ..... | H01J 37/3244 |

OTHER PUBLICATIONS

Chingsungnoen et al., (2018) Antimicrobial Treatment of *Escherichia coli* and *Staphylococcus aureus* in Herbal Tea Using Low-Temperature Plasma. J Food Prot 81(9): 1503-1507.

Hertwig et al., (2015) Impact of remote plasma treatment on natural microbial load and quality parameters of selected herbs and spices. Journal of Food Engineering 167(Part A): 12-17.

Hertwig et al., (2018) Cold atmospheric pressure plasma and low energy electron beam as alternative nonthermal decontamination technologies for dry food surfaces: A review. Trends in Food Science & Technology 77: 131-142.

Hong et al., (2009) Sterilization effect of atmospheric plasma on *Escherichia coli* and *Bacillus subtilis* endospores. Lett Appl Microbiol 48(1): 33-37.

Kim et al., (2014) Microbial decontamination of red pepper powder by cold plasma. Food Microbiol 38: 128-136.

Man et al., (2016) Health Threats from Contamination of Spices Commercialized in Romania: Risks of Fungal and Bacterial Infections. Endocr Metab Immune Disord Drug Targets 16(3); 8 pages.

Pauly and Paszkiewicz (2011) Cigarette smoke, bacteria, mold, microbial toxins, and chronic lung inflammation. J Oncol 2011: 819129; 14 pages.

Ruchlemer et al., (2015) Inhaled medicinal cannabis and the immunocompromised patient. Support Care Cancer 23(3): 819-822.

CeraPlas™ piezo plasma generator; Cold plasma from a single component [Oct. 31, 2014]. Retrieved from: https://www.tdk-electronics.tdk.com/en/373562/tech-library/articles/applications-cases/applications-cases/cold-plasma-from-a-single-component/1109546, on Nov. 11, 2020. 6 pages.

Piezoelectric Transformer, Inverter Module; Multi-layered Rosen Type Transformer. Nihon Ceratec Co., Ltd. Retrieved from: http://www.ceratecinc.com/pdf/transformer/PiezoelectricTransformer_InverterModule.pdf, on Nov. 17, 2020; 6 pages.

\* cited by examiner

DEVICE AND METHOD FOR HERBS DISINFECTION

FIELD OF THE INVENTION

The invention, in some embodiments, relates to the field of disinfection herbs by plasma.

BACKGROUND OF THE INVENTION

Plasma refers herein to ionized fluid, including positively charged ions and negatively charged electrons, wherein the whole volume of the ionized fluid is roughly neutral. Positively charged ions and negatively charged electrons are generally referred to herein as "ions" and "electrons" respectively. Neutral atoms and molecules are referred to as "neutrals". Non-thermal (or "cold") plasma refers to plasma wherein the neutrals' temperature, dictated by the neutrals' average random velocity, is low, e.g. below about 55 degrees C. or even below about 40 degrees C. [Do we want to include heating by plasma?]

Herbs herein may include any product from plants (herein including mushrooms) in the form of granular material including chunks, small pieces, particles or even powder, and are meant to include spices. Such herbs may be produced from various parts of the plant—alone or mixed together in combinations—such as from leaves or stems, possibly, but not necessarily crushed or dried and grinded; from flowers and inflorescence, in whole or after drying and chopping or crushing; grains or seeds, grinded or not; from fruits and berries, roots or bark etc., possibly in whole (particularly if in small dimensions) or alternatively chopped to pieces or grinded. Such herbs may be provided and/or consumed relatively fresh, within hours or days after harvesting, or, additionally or alternatively, may be supplied and/or consumed weeks or months after harvesting (consuming herein includes eating, drinking, smoking, inhaling and any other way of exploiting and consuming herbs for personal use). Herbs may possibly (but not necessarily) be consumed after being processed, for instance to facilitate packaging, or preservation or consuming etc. Such processing prior to consuming (performed either by a manufacturer or a supplier or the consumer) may include for instance any one or a combination of steps such as drying, baking, cooking, grinding or crushing—to name a few.

Recognition of hazardous infectious bacteria and fungi on herbs have grown considerably in recent years. Betts (International Food Hygiene, Vol. 25 No. 1 (2015) P 11, http://www.positiveaction.info/pdfs/articles/fh25_1p9.pdf) quotes a report to the UK Advisory Committee on the Microbiological Safety of Foods in 2008, reporting that the *Salmonella* contamination rate of dried herbs and spices could be between 0.6% and 14%, with UK samples being contaminated at a rate of 1%. In further surveys conducted in the USA, the FDA sampled 2,844 imported dry spice shipments from 2007 through 2009 and found about 7% contained *Salmonella*, twice the rate of other FDA regulated food products.

Betts concludes that due to their methods of production, herbs and spices are often contaminated with a wide variety of micro-organisms, some may be considered human pathogens.

Man et. al. ("*Health Threats from Contamination of Spices Commercialized in Romania: Risks of Fungal and Bacterial Infections*", Endocr. Metab. Immune Disord. Drug Targets. 2016, 16(3), 197-204) found that fungi were observed in 72.7% of black pepper samples, 33.3% in white pepper, 30% in sweet chili and 25% in hot chili products. The most common isolated fungus was *Aspergillus* spp., while *Rhizopus, Mucor, Fusarium, Penicillium* and *Absidia* species were also found in smaller percentage.

In a review study regarding tobacco ("*Cigarette Smoke, Bacteria, Mold, Microbial* Toxins, and *Chronic Lung Inflammation*", Journal of Oncology Volume 2011 (2011), Article ID 819129), Pauly and Paszkiewicz argue that tobacco companies have identified and quantified bacteria, fungi, and microbial toxins at harvest, throughout fermentation, and during storage. Yet, the authors also note that ample information has accumulated to suggest that microbes and microbial-derived factors may contribute to the health risks of smoking and smokeless tobacco products. Moreover, the microbes may facilitate microbial colonization of the mouth and airway, the induction of chronic inflammation through the activation of diverse leukocyte subsets, alteration of the tissue microenvironment, and microbial-toxin-induced pathologies. The authors conclude that tobacco products should be assessed with the knowledge that they contain bacteria, mold, and microbial toxins.

The case of *Cannabis* is particularly important, because medical *Cannabis* is often recommended or even prescribed to people in various stages of compromised health, that might therefore be more vulnerable than healthy people to pathogens. Ruchlemer et. al. ("*Inhaled medicinal Cannabis and the immunocompromised patient*", Support Care Cancer (2014), DOI 10.1007/s00520-014-2429-3) list some 10 references describing the detrimental effects of inhaled *Aspergillus* via *Cannabis* among patients, most of whom were immunocompromised. In some of those cases, the outcome was fatal. The research aimed to identify the safest way of using medicinal *Cannabis* in immunosuppressed patients by finding the optimal method of sterilization with minimal loss of activity of *Cannabis*. The authors have found plasma sterilization to be effective and causing the least quantitative loss of the active *Cannabis* compound A9-THC, and argue that systematic sterilization of medicinal *Cannabis* can eliminate the risk of fatal opportunistic infections associated with *Cannabis* among patients at risk.

Plasma-assisted sterilization (e.g. of medical instruments or food packages) is known, and is typically characterized by sterilizing at low temperatures objects that could be damaged by high temperature sterilization processes such as steam sterilization for example. Typical low-temperature plasma sterilizers employ hydrogen peroxide ($H_2O_2$) as a precursor for the active species. $H_2O_2$ may be added to the plasma chamber in a liquid form and following evaporation and diffusion in the space of the chamber, plasma-induced ions and free radicals originating from the $H_2O_2$ employ the organisms extermination. However, such use of plasma-assisted $H_2O_2$ sterilization may be regulated and restricted in some countries of the world in terms of the objects that may be sterilized, the concentrations allowed to be used and the means and time that should be applied after use so as to verify sufficient disintegration to prevent health risks for a user. Thus, such sterilization processes that employ hydrogen peroxide may be considered less than optimal or even prohibited for sterilizing food or herbs, particularly. in domestic use.

Hertwig et al ("Impact of remote plasma treatment on natural microbial load and quality parameters of selected herbs and spices" J. of Food Eng. P. 12, Vol. 167, 2015) investigated the decontamination efficiency of a non-thermal remote plasma application for dry and heat-sensitive products (pepper seeds, crushed oregano and paprika powder). In the experiment, plasma-processed-air (PPA) was used to decontaminate the tested herbs. The PPA was generated by a microwave driven plasma discharge set-up, working with compressed air and a gas flow of 18 SLM (standard liters per minute). The frequency of the microwave was 2.45 GHz and the power consumption was in the range of 1.2 KW. Due to the high power consumption the microwave plasma torch was ignited for 7 seconds following a break of 5 seconds. The generated microwave plasma had a peak temperature of about 3,700 deg. C. However only the generated PPA was used, which was cooled down to 120 deg. C. During collection in a concentration bottle, the PPA was cooled further down to ensure a treatment temperature of about 22 deg. C., at ambient pressure conditions. 5 gr of herbs in a bottle of 300 cc were exposed to the PPA for periods of 30 min., 60 min. and 90 minutes and generally showed convincing decontamination.

Kim et al ("Microbial decontamination of red pepper powder by cold plasma", Food Microbiology, P. 128, Vol. 38, 2014) investigated the effects of microwave-powered cold plasma treatment (CPT) on inhibition of microorganisms in red pepper powder, sometimes with combination of heat. The plasma system consisted of a magnetron for producing a 2.45 GHz wave discharge in a range of 300-900 W power level, a cooling system flowing water at 0.8 m3/min, a stainless steel treatment chamber, a gas mass flow rate controller, a vacuum pump, and a parameter controller. The plasma-forming gas, nitrogen (N2) or the mixture of helium (He) and oxygen (O2), was flowed at a maximum of 20 standard liter/min (slm). The pressure in the chamber ranges from 500 to 30,000 Pa. Moderate disinfection was achieved after treatment of 20-30 minutes, in combination with heat treatment.

Some additional solutions have been proposed to sterilize food powder using plasma. U.S. Pat. No. 8,771,595 discloses systems and methods for plasma sterilization wherein the method includes placing a substance to be sterilized in a rotating chamber (e.g., drum) and exposing the substance to a radio frequency (RF) plasma. The mixing of the substance and plasma is further promoted by generating a magnetic field that produces a force on the substance in a direction opposite to the rotational direction of the chamber.

SUMMARY OF THE INVENTION

Some aspects of the invention relate to disinfection of herbs by plasma, and more specifically but not exclusively, to devices and methods for disinfecting herbs in small quantities, e.g. for home or personal use.

Disinfecting food, and particularly disinfecting herbs, is different in several aspects from disinfecting inanimate articles (such as, for example, medical devices). Food and herbs are much more sensitive and can be easily modified or damaged or even disintegrated, if subjected to typical sterilization procedures that are suitable for items made of plastics, glass or metal, e.g. processes that involve high temperatures and/or high pressure. Radiation-based techniques (e.g. gamma-ray radiation) may also be inadequate or less than optimal for food, because the radiation might also damage the food, and because these method are typically more expensive than alternative methods. Using disinfectants is also limited or totally prohibited, because disinfectants might be adsorbed or absorbed in the food and may pose difficulty to remove to a sufficient degree after applying.

In contrast to the above-described methods, cold plasma may be highly effective in disinfecting herbs, while preserving all or at least most of the herbs characteristics and ingredients. In the study quoted above, Ruchlemer et. al. have demonstrated that using cold plasma was very effective in disinfecting *Cannabis* herbs, while causing the least quantitative loss of the active *Cannabis* compound A9-THC. Generally, disinfection is effected due to active molecules that are generated during ionization of low-pressure air (with or without addition of inert gases such as helium or argon) and their destructive effect on living organisms. Such active molecules or atoms may include for example NO, O, CO, H and others. If He is introduced to the gaseous mixture, then excited He may also be found in the gas following ionization. Moreover, if sources of hydrogen atoms are present— for example if the ionized gas includes water vapor—then OH— may also be found following ionization. Experiments, some of which are detailed further below, show that exposure of herbs infected by bacteria or fungi to the active gaseous mixture obtained following plasma generation as described herein, results in extermination or at least substantial reduction of the infectious species and hence disinfects the herbs. Required exposure duration is less than 10 minutes, and typically even less than 5 minutes. It is noted that introduction of hydrogen peroxide ($H_2O_2$) related additives to the gaseous mixture prior to plasma generation may in some embodiments enhance and expedite the extermination of bacteria and fungi; however in preferred embodiments, satisfactory disinfection may be obtained without such introduction of H2O2-related additives.

Generally, disinfecting an object by plasma may be carried out according to two different schemes. In one scheme (termed here "indirect") the plasma is generated (that is to say the gas is ionized) in one region while the object to be treated is positioned in a different region, where ionization does not occur. According to this scheme, gas is either made to flow, or allowed to diffuse, from the region of ionization to the region where the treated object is located. According to the second scheme (termed here "direct"), the object to be treated is positioned substantially within the region where ionization takes place, e.g. in a region between two or more electrodes where an electric or electromagnetic field is applied to ionize the gas. The two described schemes have different characteristics, and from a practical point of view, each has some advantages (and obviously disadvantages) relative to the other.

It is first noted that ionized gas includes various types of active species having, generally, various time constants for decay. For example, positively charged ions and negative charge electrons, generated by the excitation and ionization of initially neutral atoms and molecules, may recombine over a time scale shorter than a millisecond, e.g. on the order of magnitude of microseconds. Likewise, relaxation of excited atoms and molecules typically occur over time scales shorter than milliseconds. Recombination of electrons and ions, as well as relaxation of excited atoms and molecules, typically involve emission of light, hence the region where recombination and relaxation occurs is typically characterized by light emission (glow). After recombination and relaxation, the gas that was ionized may generally include also active species—predominantly active molecules—which recombine or decay or decompose over times longer than ion-electron recombination and relaxation times, e.g. up to an order of magnitude of seconds or more, such as some types of free radicals. Thus, when plasma is generated at a distance from a region to be treated, and then the excited gas is guided towards that region, only active species that decay over relatively long times may survive the travel and affect the treated region. Species with decay times shorter than the travel time from the plasma generation region to the treatment region may decay during the travel, and consequently may not contribute to treatment. Moreover, electron-ion recombination is often accompanied by excess emission of UV light, which is also an effective disinfectant. Accordingly, when plasma is generated in the treatment region and within line of sight with treatment surfaces, such UV light may contribute to disinfection. If however plasma is generated at a distance from the treatment region, and/or with no lien of sight with surfaces to be treated, then UV light may not participate in the disinfection process.

Thus, applying a direct scheme of plasma treatment, namely generating plasma around or in the immediate vicinity of the treated object or material, provides an excess of radiation and highly excited species—including ions and electrons—in the immediate vicinity of the object's surface. Consequently, the effects on the objects surface are typically more intense and evolve faster in the direct scheme. Particularly, disinfection is quicker and more effective in the direct scheme. However, generating plasma in the immediate vicinity of herbs, e.g. in the form of small pieces or powder, may be unpredictable in some cases, difficult to employ, or impossible altogether. Since plasma generation—gas ionization—in a given region is achieved by applying strong electric or electromagnetic (EM) fields across that region, any object placed in the effected region may alter the fields, sometimes in unpredictable manners. For example, the effect of a pile of herbs placed in between two electrodes applying a plasma-generating EM field therebetween, may depend on a combination of factors, including for example the size and shape of the pile of herbs and the exact location thereof relative to the electrodes, the dimensions of the pieces or particles that make up the pile, the air gaps between the particles, and the electrical conductivity of the particles, just to name a few such factors. For example, two samples of the same herb that are similar in overall quantity and sizes, but having different levels of moisture (e.g. one sample is dried and the other is not)—may cause very different results when placed in a region where plasma-generating EM field is applied. In some cases, for example, the moist powder will facilitate arcing, forming together a high conductivity trajectory between electrodes, and thereby prevent the formation of stable glow discharge, that may be required for the desired plasma generation. As another example, two samples of the same herb, similar to one another, may also cause very different behavior of plasma, if one sample is treated while being placed still as a pile, whereas the other sample is treated while being maintained floating in the space between the electrodes (e.g. by a mixer or a fan).

Accordingly, an indirect scheme, wherein plasma is generated distantly from the treated material, typically offers a more predictable work point compared to the direct scheme. Because the plasma is generated in a region void of the treated material, plasma generation is typically dependent only on the operational parameters (such as the spatial arrangement and geometry of the electrodes and electromagnetic power and frequency supplied to the electrodes), and hence is more easily predictable and controllable. However, after ionization the excited gas must be directed or allowed to flow or to diffuse towards the treated material. Consequently, some of the excited molecules and active species decay during the travel as explained above, resulting in exposure of the treated material to a smaller variety and smaller concentration thereof. Further, the treated object is, generally, not exposed to UV light in this scheme and thus the indirect scheme ultimately, results in a possibly less intense treatment, compared to the direct scheme. These drawbacks are clearly demonstrated in the publications of Hertwig et. al. and Kim e. al. discussed above, which employ an extreme indirect scheme where plasma is generated at high power distantly from the treatment chamber, and plasma-treated-air or plasma-treated-gas is driven to the treatment chamber following cooling. Moderate to satisfactory disinfection was usually obtained when several grams of herbs were treated for tens of minutes (20 or 30 or even more) and at typical plasma power consumption of hundreds of Watts. In some cases additional direct heat treatment was required to further the disinfection.

It may therefore be concluded that selecting the direct scheme or the indirect scheme may be dependent on several factors, some of them may be gained or clarified through trial and error. It is typically expected that the direct scheme may provide a more intense—and hence a faster—process, but may involve a higher likelihood—risk—of unpredicted results, or may be impossible to implement. It is further concluded that if the indirect scheme is adopted, the closer the plasma generation region is to the location of the treated material—and the shorter line of sight is maintained between the plasma generation region and the treated surface—the higher the effectiveness of the treatment is expected to be.

Disinfecting food—and more particularly disinfecting herbs—in small quantities at home by the intended consumer, is significantly different and in some aspects advantageous over industrialized sterilization or disinfection processes that are carried out on large quantities by a manufacturer or a distributor. One advantage to the consumer results from the confidence of the consumer that the herbs are indeed disinfected, instead of relying on presumed disinfection processes that are carried out—or not—by others. This advantage is particularly important when the herbs in question come from less regulated countries like third-world countries, or belong to less regulated fields—like *Cannabis* for instance. In cases when a consumed herb originates from a questionable source, characterized with unknown or uncertain processing, disinfection at home may considerably reduce the uncertainty.

A second advantage results from the relatively short time periods between disinfection and consuming when disinfection is carried out at home, compared to the long time periods that might be involved in some cases between industrialized disinfection in the factory and eventual consuming. After disinfection is carried out at the factory, even when disinfection was proper, infectious bacteria and/or fungi might accumulate again on the herbs, especially if storage is long and under inadequate conditions. Disinfection at home, shortly before consuming, may thus remove any such infectious bacteria and/or fungi, leaving the herb undoubtedly disinfected prior to consuming.

Yet another advantage of disinfecting small quantities of herbs results from the dependency of the ratio of surface area to volume of the treated herbs, on the quantity of herbs being treated. As the total quantity of material—particles or powder etc.—to be treated decreases, the percentage of surface area of that material that is directly exposed to active gas species, increases (that is, assuming the material is provided as a pile of some shape, rather than being dispersed). Since disinfection—destroying bacteria and fungi—occurs mainly or even solely on the surface of the treated particles, the greater the percentage of surface area that is directly exposed to active gas species and to UV light, the shorter the plasma generation time should be and the higher the effectiveness of the treatment is. The term "directly exposed to active gas species" herein refers to those particles in a pile that are disposed on the outskirts of the pile, particularly those that are facing the source of the plasma. The reason for a difference in the effect the active gas may have on particles directly exposed to it compared to particles that are, for example, buried inside the pile, is twice- or even three-fold: First, particles of the material that do not have line of sight with the plasma generation region, are not exposed to UV light. Second, in embodiments of the direct scheme mentioned above, particles on the outskirts of the pile may be directly exposed to ions and free electrons prior to recombination, which contribute immensely to intensifying the disinfection process. And third, excited species and active molecules may more likely decompose or decay before reaching the depth of pile, compared to reaching the pile's outskirts. A gas molecule's trajectory to reach inside the pile is evidently longer than reaching the pile's outskirts and hence takes more time. Moreover, reaching inside the pile may involve on the average more interactions with herbs particles, and hence higher likelihood to decay.

To give a non-limiting numerical example: 10 gr of black pepper consists of about 200-300 individual grains (each being roughly a sphere of 2-4 mm in diameter), that may build up about 2 layers of grains on the bottom of an ordinary cup. Thus, a quantity of 10 gr or a couple of 10s of grams of grains such as black pepper, may be treated by plasma in a vessel the size of about an ordinary cup, where practically the entire surface area of the grains is directly exposed to the active gas species. As another example a case of much smaller particles may be considered: A quantity of 1 gr of herbs particles in the forms of platelets, each with an average area of about 1 $mm^2$ and thickness of 0.1 mm may consist roughly about $2*10^4$ particles (assuming a specific weight of 0.5 gr/cm3), that cover an area of 100 $cm^2$ if spread evenly in 2 layers on the average. In other words, a quantity of 1 gr of herbs crushed to small pieces (e.g. grinded leaves) may be plasma disinfected in a vessel having a floor surface of 10×10 cm, the particles forming on the vessel floor a double layer on the average, thus being significantly, if not entirely, directly exposed to the active gas and to UV light (if plasma is generated on both sides of the layers).

It should be evident to the person skilled in the art that similar levels of direct exposure to active gas cannot be attained practically when commercial or industrial quantities of material should be disinfected. For example, even a relatively small quantity (on industrial scale) of 10 Kgr of black pepper grains arranged in two layers cover an area of roughly 3 $m^2$, which is prohibitive, or at least highly ineffective to implement. If, on the other hand, such amount is arranged as a more compact and less dispersed pile, the likelihood for an active molecule reaching the depth of the pile may be considerably lower. Thus, stirring or mixing might be a must when plasma-treating large industrial quantities, to allow for particles deep inside a pile of herbs to reach the outskirts of the pile to obtain satisfactory uniformity of disinfection.

It is thus concluded that plasma treating relatively small quantities of herbs, that may be suitable for home use, on the order of a few grams or a few tens of grams at most, may be accomplished in a relatively short time of a few minutes, by way of directly exposing the great majority of the material—if not all the material—to active gas, and possibly to UV light, in a relatively small device. Such disinfection may be thus accomplished, in some embodiments, with no need to mix or stir the powder. In some embodiments satisfactory disinfection may require shaking or vibrating the herbs, which can even be done by hand or by a tap of a finger and additionally or alternatively by a vibrator, the vibrator being inclusive in the device or external to it. It is noted that mixing or stirring, on the other hand, may not be effected practically by means that are external to the disinfection device, even when treating small quantities. It is thus concluded that obtaining a satisfactory uniform disinfection without a stirrer or a mixer is a further possible advantage according some embodiments of the invention.

Yet a further advantage of disinfecting small quantities of herbs emerges from the small dimensions of the device used for generating the plasma and the vessel in which herbs (in a quantity weighing typically up to a couple of tens of grams) are sited during disinfection. As explained above, a few grams—or a few tens of grams at most—of herbs occupy a volume of a couple of tens of cubic centimeters at most—as a non-limiting illustration, a 1 cm thick layer on the floor of a vessel the size of an ordinary cup may be imagined. The relatively small volume of the intended treatment region allows employing, at high efficiency and effectiveness, any one of the direct scheme and the indirect scheme as described above. If the direct scheme is selected, plasma must be generated over a volume of some 10 or 20 cubic cm and across distances of the order of several centimeters at most. It is noted that generating plasma in such conditions may be readily accomplished using any one of a variety of configurations and operational parameters, as is described and explained further below. Moreover, if the indirect scheme is selected, plasma may be generated substantially adjacently, if not adjoining, the treatment region. For example, plasma may be generated at typical distances of a few centimeters, and below 7 cm at most from where the herbs are positioned. It is emphasized that such a characterization means that any point in the treatment region—namely every piece of a treated herb—lies at a distance not greater than 1 or 2 or 5 cm, or even less that 7 cm at most, from where plasma is generated. In such configurations the treated material may be exposed to a relatively highly excited gas, or at least to gas containing relatively high concentration of active molecules as explained in detailed above, and therefore the plasma treatment is expected to be relatively intense and effective.

There is therefore provided, according an aspect of the invention, a device for disinfecting herbs using plasma, wherein the device comprises a sealable vessel dimensioned and configured to contain powder or particles of herbs in a treatment region of the sealable vessel; a power source configured to generate electromagnetic (EM) power sufficient for plasma generation; and at least one electrode, electrically associated with the power source and positioned and configured to apply a plasma-generating EM field in a plasma generation region inside the sealable vessel upon receiving from the power source plasma generating power.

Certain embodiments of the present invention may include some, all, or none of the above advantages. Further advantages may be readily apparent to those skilled in the art from the figures, descriptions, and claims included herein. Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

The principles, uses and implementations of the teachings herein may be better understood with reference to the accompanying description and figures. Upon perusal of the description and figures present herein, one skilled in the art is able to implement the teachings herein without undue effort or experimentation.

Figure 1:
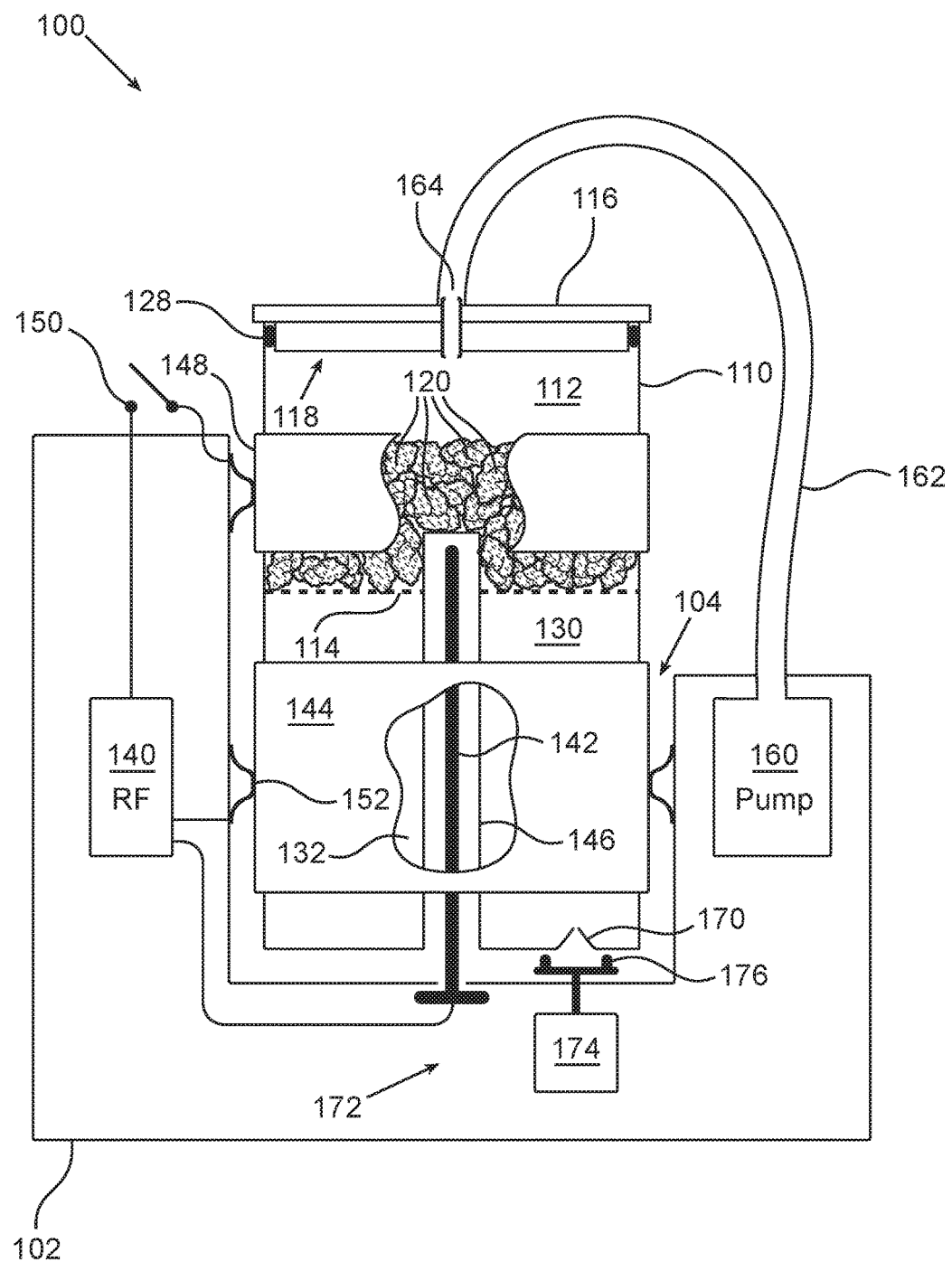
FIG. 1 schematically depicts an embodiment of a device for disinfecting herbs in a sealable vessel, using plasma, according to an aspect of the invention.

FIG. 1 schematically depicts an embodiment of a device 100 for disinfecting herbs according to an aspect of the invention. Device 100 comprises a plasma excitation device 102 and a sealable vessel 110, generally made from a dielectric material such as glass, Poly(methyl methacrylate) (Perspex®) or another suitable plastic material. In some embodiments however, the sealable vessel or significant part thereof may be made of metal. According to some embodiments, as is exemplified in FIG. 1, sealable vessel 110 is detachable from plasma excitation device 102, and plasma excitation device 102 comprises a slot 104 configured to house sealable vessel 110 during operation.

The internal volume of sealable vessel 110 comprises a treatment region 112, defined between a net 114, the vessel's walls and a top cover 116. Sealable vessel 110 may be opened by a user by removing top cover 116 from a top opening 118 of the sealable vessel, e.g. for disposing herbs for treatment in treatment region 112 and for removing the disinfected herbs following plasma disinfection. Top cover 116 is configured to seal sealable vessel 110 upon closing, by a seal 128 (e.g. an O-ring). Treatment region 112 is dimensioned and configured to contain herbs 120 in a form of chunks or grains or particles or powder or any other form of small pieces typical of herbs or spices, in a small quantity of several tens of grams at most, suitable for home or personal use.

Net 114 separates treatment region 112 from a bottom portion 130 of the internal volume of sealable vessel 110, wherein bottom portion 130 may function as a plasma generation region 132 or as a part thereof. Net 114 is configured as a porous sheet, permeable to gas but impermeable to herbs contained in treatment region 112. In other words, net 114 is configured to allow gas to flow or to diffuse between bottom portion 130 and treatment region 112, but to prevent penetration or infiltration of herbs from the treatment region 112 to the bottom portion 130. Net 114 may be made from a dielectric material such as nylon or plastic (e.g. polyurethane) or glass, and may be flexible or rigid. According to some embodiments, net 114 may be made of an electrically conducting material—e.g. as a metallic net or a thin, finely perforated metal sheet, being possibly used as an electrode in the plasma-generating circuitry. According to some embodiments net 114 is detachable from the sealable vessel, allowing a user removing the net from the vessel, e.g. for rinsing the net and for accessing the bottom region 130, e.g. for cleaning it.

Plasma excitation device 102 comprises a RF (radio-frequency) power source 140 configured to produce a RF electromagnetic (EM) power at high voltage sufficient to ionize gas and generate plasma. Power source 140 is electrically associated with a central electrode 142 shaped as a thin rod extending from plasma excitation device 102 into slot 104 and into bottom portion 130. Power source 140 is also electrically associated with a cylindrical electrode 144 enveloping bottom portion 130. When power source 140 is activated, a RF, plasma generating EM field is applied between central electrode 142 and cylindrical electrode 144, and plasma may be generated in the space between the electrodes.

Power source 140 may be configured to provide high voltage in the range of about KV to 15 KV, and even between about 3K to 30 KV. It should be understood that the voltage required for plasma excitation may not be determined with certainty, hence a suitable voltage may be selected from within a relatively wide range. One reason is that the plasma generating EM field is determined by a combination of parameters, the RF voltage being only one among several. Additional parameters affecting the field may include the spatial arrangement of the electrodes and distances between them; the quantity and spatial distribution of the treated herbs (if the herbs are near or in between the electrodes), moisture of the herbs etc. Moreover, plasma may be excited at different field strengths, depending on the gaseous composition and pressure in the vessel. Furthermore the field frequency, determined by the voltage frequency, also affects plasma excitation. Typically, a very wide range of frequencies may be used, between 10 KH and 100 MH and even up to about 1 GHz. It is noted in this regard that the term RF is used herein in a very broad sense referring substantially to an AC signal. It is therefore concluded that the range of voltages specified above is generally suitable for plasma excitation in a vessel of typical size of a few centimeters, yet the voltage supplied by the power source should be ultimately determined by some degree of trial and error, and may even deviate from the ranges specified above in some cases.

To maintain generation of cold plasma—that is to say, to maintain the temperature of the excited gas and the immediate surroundings below a pre-determine value, e.g., 40 Degrees C., the average power supplied by the power source should advantageously be regulated. According to some embodiments the average power supplied by power source 140 is regulated by pulse-modulating the power supply to the electrodes and controlling the duty cycle of the modulation. Typical modulation frequency may be in the range of 10 Hz-1 KHz, although modulation frequency may be selected in some cases outside this range. Modulation duty cycle may typically be in the range of 1%-90%, although modulation duty cycle may be selected in some cases outside this range. Controlling the duty cycle of pulse modulation of the supplied power allows for linear and reliable control of the average power supplied, thus allowing for higher energetical efficiency of the device, and rendering a cooling system unnecessary.

The plasma generation region 132 is the region in which plasma is generated when the power source is activated, and generally corresponds to the space between the electrodes applying the EM field. In some embodiments the plasma generation region 132 overlaps with the bottom region 130. In some embodiments the plasma generation region 132 is smaller than the bottom region 130, so as to allow a separating space between the plasma generation region 132 and the treatment region 112 that occupies the herbs. The separating space in such embodiments thus dictates a minimum non-zero distance between the herbs and where plasma is actually generated. According to some embodiments, the plasma generation region 132 may overlap, partially or entirely with the treatment region 112. In other words, plasma may be generated in such embodiments within a part of treatment region 112 or within the entirety thereof.

As is exemplified in FIG. 1, the central electrode 142 extends partially above net 114 and hence into the treatment region 112. Consequently, plasma may be excited in the embodiment of FIG. 1 also in some of the space occupied by herbs 120. For restricting the plasma generation to the bottom region 130 only—that is to say, to prevent plasma generation in any portion of treatment region 112—the central electrode 146 may be configured shorter, so as not to penetrate above net 114, into treatment region 112. In some embodiments it may be desired to ensure plasma generation in part or in the entirety of treatment region 112. This may be accomplished by employing one or more additional cylindrical electrode 148, enwrapping the treatment region. The additional cylindrical electrode 148 may be electrically associated with power source 140 or connected directly to cylindrical electrode 144. In some embodiments such electrical association may be executed via a switch 150 so as to allow controlled connection and disconnection of the electrode with the power source, thereby controlling generating plasma, or not, respectively, in the treatment region 112 (that is to say, generating plasma in the direct or in the indirect scheme, respectively).

Central electrode 142 is electrically insulated from the gas inside bottom portion 130 by a blind sleeve 146. According to some embodiments, as is exemplified in FIG. 1, central electrode 142 is fixed to plasma excitation device 102, being electrically connected with power source 140. Central electrode 142 extrudes into slot 104, and blind sleeve 146 is shaped as an elongated narrow depression of the floor of sealable vessel 110, depressed into the vessel and dimensioned to envelope central electrode 142. Hence, when sealable vessel 110 is positioned in slot 104, central electrode 142 is enveloped by blind sleeve 146. According to some embodiments the central electrode may be attached to the sealable vessel being thereby detachable from the plasma excitation device 102. In such embodiments the central electrode may electrically associate with power source 140 via an electrical contact in slot 104 upon positioning the sealable vessel in the slot.

Cylindrical electrode 144 is electrically insulated from the gas inside bottom portion 130 being wrapped around the wall of sealable vessel 110 on the external surface thereof. According to some embodiments, as is exemplified in FIG. 1, cylindrical electrode 144 is fixed to the sealable vessel, whereas device 100 comprises a cylindrical electrode contact 152, electrically associated with power source 140. When sealable vessel 110 is positioned in slot 104, cylindrical electrode contact 152 contacts cylindrical electrode 144, thereby electrically associating the electrode with the power source. It is noted that according to some embodiments the cylindrical electrode may be detached from the sealable vessel, e.g. may be fixed inside the slot 104 being constantly connected with the power source. In such embodiments disposing the sealable vessel in the slot positions the cylindrical electrode in an enveloping configuration around the bottom portion 130 of the sealable vessel, thereby enabling the production of a plasma generating EM field in the bottom portion 130 between the central electrode and the cylindrical electrode as described above, when the power source is activated.

It is noted that according to some embodiments, the central electrode and/or the cylindrical electrode may not be insulated from the gas inside the sealable vessel. For example, the sealable vessel may comprise a conducting rod exposed to the gas inside the sealable vessel, such conducting rod being electrically associated with an electric contact outside the sealable vessel. Likewise, the cylindrical electrode may in some embodiments comprise an exposed (not insulated) conducting cylinder on the inner surface of the sealable vessel's walls. Additionally or alternatively, plasma may be generated in the vessel in a capacitively coupled plasma (CCP) mode of operation, wherein the electrodes are capacitively coupled by the gas in the space between them. Additionally or alternatively, plasma may be generated in the vessel in a dielectric barrier discharge (DBD) mode of operation, wherein a dielectric insulation separates between the electrodes. Such a dielectric insulation may comprise walls of the sealable vessel, or be shaped as dielectric coating to one of the electrodes or to both, or even as a dielectric sheet blocking line of sight between the electrodes.

Typically, if all other factors are similar, plasma may be generated more easily (that is to say, plasma may be ignited at a lower voltage) when the dielectric potential barrier between the electrodes is lower. Hence, when both electrodes are exposed to the gas inside the vessel, plasma may be ignited relatively easily compared to embodiments comprising a dielectric insulation between the electrodes. However when at least one of the electrodes is insulated, plasma may be generated more uniformly compared to embodiments where the two electrodes are exposed, and the risk of arcing is lower. The risk of arcing or non-uniform, or highly localized plasma generation even increases in the presence of objects or particles in the space between the electrodes. Hence the selection of a preferred mode of plasma generation may be done by considering the geometrical configuration of the electrodes, the space and distance between them, and the risk of penetration of dirt (e.g. powdered debris from the herbs) into that space.

It is further noted that plasma may be generated in the plasma generation region of the sealable vessel using various electrodes configurations, and the configurations discussed above are provided as non-limiting examples only. Some further examples may include generating plasma between two plated electrodes, e.g. one at the bottom of the plasma generating region and the other across from the first, at the top of the plasma generating region. In some embodiments, a metallic net 114 may be used as one of the electrodes. According to some embodiments, plasma may further be generated in an inductive coupled plasma (ICP) mode of operation, using one or more conducting spirals around the vessel (e.g. outside the vessel's walls or inside the vessel) as electrodes. Some of these exemplary electrodes configurations are schematically depicted in the next figures, however it should be understood to the person skilled in the art that, generally, none of the embodiments necessitates a particular electrode configuration, so each embodiments may be equipped with each of the electrode configuration described in the specification, subject to necessary adjustments.

It is further noted that according to some embodiments electrical association of any of the electrodes—for example the central electrode and/or the cylindrical electrode of FIG. 1—with the power source 140 may comprise capacitive or inductive coupling, in addition or instead of galvanic (electrical) contact.

It is yet further noted that plasma excitation in the plasma generation region may be employed using a piezoelectric element (PE) used as a HV transformer. Typically, such a PE may be configured and operable to transform a RF, low-voltage signal, supplied to a low-voltage portion of the piezoelectric element, to a RF, high-voltage signal, which is generated at a high-voltage end of the piezoelectric element. In operation, the high voltage at the high voltage end of the PE may suffice to apply a plasma-generating EM field in the surroundings of the high voltage end. Suitable piezoelectric elements may be commercially provided, for example, by Nihon Ceratec Co. Ltd. (http://www.ceratecinc.com/pdf/transformer/Piezoelectric Transformer_InverterModule.pdf), and by EPCOS AG (https://en.tdk.eu/tdk-en/373562/tech-library/articles/applications---cases/applications---cases/cold-plasma-from-a-single-component/1109546). In the schematic depiction of FIG. 1, such a PE and a corresponding low voltage power source for supplying LV RF signal thereto, may, according to some embodiments, take the place of central electrode 142 and power supply 140, respectively. In such a scheme power source 140 supplies a RF low voltage signal to a low voltage portion of the PE element, located generally in the bottom part of the element, yielding high voltage generation at the high voltage end of the PE, at the top end thereof. It is further noted that a PE as described herein may be used, mutatis mutandis, instead of a high voltage electrode in any of the embodiments described herein.

Plasma excitation device 102 may further comprise a gas pump 160 fluidly associated with the internal volume of sealable vessel 110 via a tube 162 and a pumping port 164 in top cover 116. Pump 160 may be configured to pump air from sealable vessel 110 so as to reduce the pressure therein down to below about 0.5 bar, or below about 0.2 bar or below about 0.1 bar or to below about 0.01 bar or even to below about 0.001 bar. According to some embodiments, tube 162 is connected to top cover 116 as is exemplified in FIG. 1, thereby maintaining sealable vessel 110 detachable from plasma excitation device 102 and enabling removing the vessel from the slot while top cover 116 remains connected to tube 162. Additionally or alternatively, tube 162 may be detached from pumping port 164 and sealable vessel 110 may be detached from the plasma activation device sealed with the top cover 116.

It is noted that in some embodiments plasma may be generated—and herbs may be disinfected by the resulting gaseous active species—at ambient pressure of 1 Atm., thus evading the need for a gas pump in the device. According to some such embodiments, plasma is generated in an open vessel with ambient pressure and composition. Additionally or alternatively, plasma generation may be assisted by the inflow of inert gas such as helium into the vessel towards the space between the electrodes. According to some such embodiments the device may include a gas source (not shown here) such as a pressurized gas reservoir, or the vessel may be configured to fluidly connect to such a gas source, possibly through a tube which is connected to the vessel's top cover on the one end and to the gas source on the other end thereof. The vessel may not be sealed, to prevent pressure rise therein due to the inflow of the inert gas. It is further noted however that generating plasma at ambient conditions is more difficult than generating plasma at low pressure, because operating voltage of the plasma-generating field should typically be higher, and the risk of arcing, or similar non-stable discharge effects, is higher. Plasma generation in an admixture of air and inert gas—e.g. helium—at atmospheric pressure is simpler compared to plasma generation in air, but providing a device with an inert gas source such as a helium pressurized gas reservoir, may be a less than optimal solution for a product intended for home use.

According to some embodiments sealable vessel 110 comprises a gas inlet aperture 170, for allowing controlled leakage of gas into the vessel during operation. Device 100 may further comprises a valve 172 comprising an actuator 174 and a valve seal 176, for controllably opening and closing gas inlet aperture 170. Valve 172 may be part of plasma activation device 102 as depicted in FIG. 1, or, additionally or alternatively, may be part of sealable vessel 110, having electrical contacts (not shown here) allowing the valve to be activated from the plasma activation device. Leakage of gas into the vessel during operation may be used for one or more of several objectives. In some embodiments it may considerably enhance gas transport from the plasma generation region into the treatment region, thereby enhancing the effectiveness of the plasma treatment. In device 100 for example, gas inlet aperture 170 is located at the bottom of the vessel in plasma treatment region 132, whereas gas is pumped through tube 162 which is connected to top cover 116 at the top of the vessel. As a result of gas leakage inside at the bottom of the vessel and pumped out at the top of the vessel, gas is transported effectively and quickly during operation from the plasma generation region to the treatment region. Accordingly, more active species may reach the treatment region, compared to embodiments where gas merely diffuses between the two regions.

According to some embodiments the sealable vessel may be configured to provide a direct fluid communication between the bottom region 130 and the top part of the treatment region 112, so that gas may flow from the bottom region to the top part of the treatment region without passing through the herbs 120. According to some embodiments, the net 114 may be shaped as a pot rather than as a planar sheet. The pot may be dimensioned tall enough to contain therein the entire quantity of herbs for disinfection in a single session. The pot may further be dimensioned narrow enough to have its walls distant from the walls of the vessel, so as to allow the free flow of active gas from the plasma generation region to the treatment region, while bypassing the herbs. In such embodiments, the top layer of herbs in the pot may be better exposed to active gas species, compared to embodiments wherein gas reaches the top layer of the herb only after passing through the herbs' lower layers.

According to some embodiments, controlled gas leakage into the sealable vessel may be hydrodynamically shaped as a fine jet and used to actively whirl and mix herbs 120, particularly if the herbs are in a form of fine powder. In other words, when the herbs are in the form of a fine powder, it may be expected that the herbs powder would accumulate on the floor of the treatment region in a multi-layer pile, thus diminishing the exposure of particles deep within the pile to the active species in the surrounding gas. Whirling the powder by the jet readily exposes such particles, thereby enhancing the uniformity and speed of the treatment. It may be further commented that fine gas jets formed by gas leakage into the sealable vessel as described herein may not be effective for whirling large pieces of herbs, however such mixing may be much less required when the particles are large, as explained above.

According to some embodiments device 100 may be activated using electric power from a wall outlet. Additionally or alternatively, device 100 may be activated using power from a battery or a battery pack, thus rendering the device portable. For example, disinfecting herbs at a quantity of 20 grams, say, may require plasma generation at a power consumption of between about 1 W and 10 W, and a pumping power consumption of 5-10 W, for a duration of less than 10 minutes, or less than 5 minutes, or less than 2 minutes, or even less than 1 minute. Hence, the device may be operated using, for example, four, or even a couple of AA batteries, each providing at least 2.5 Whr, for at least one, and possibly several disinfection sessions.

Figure 2:
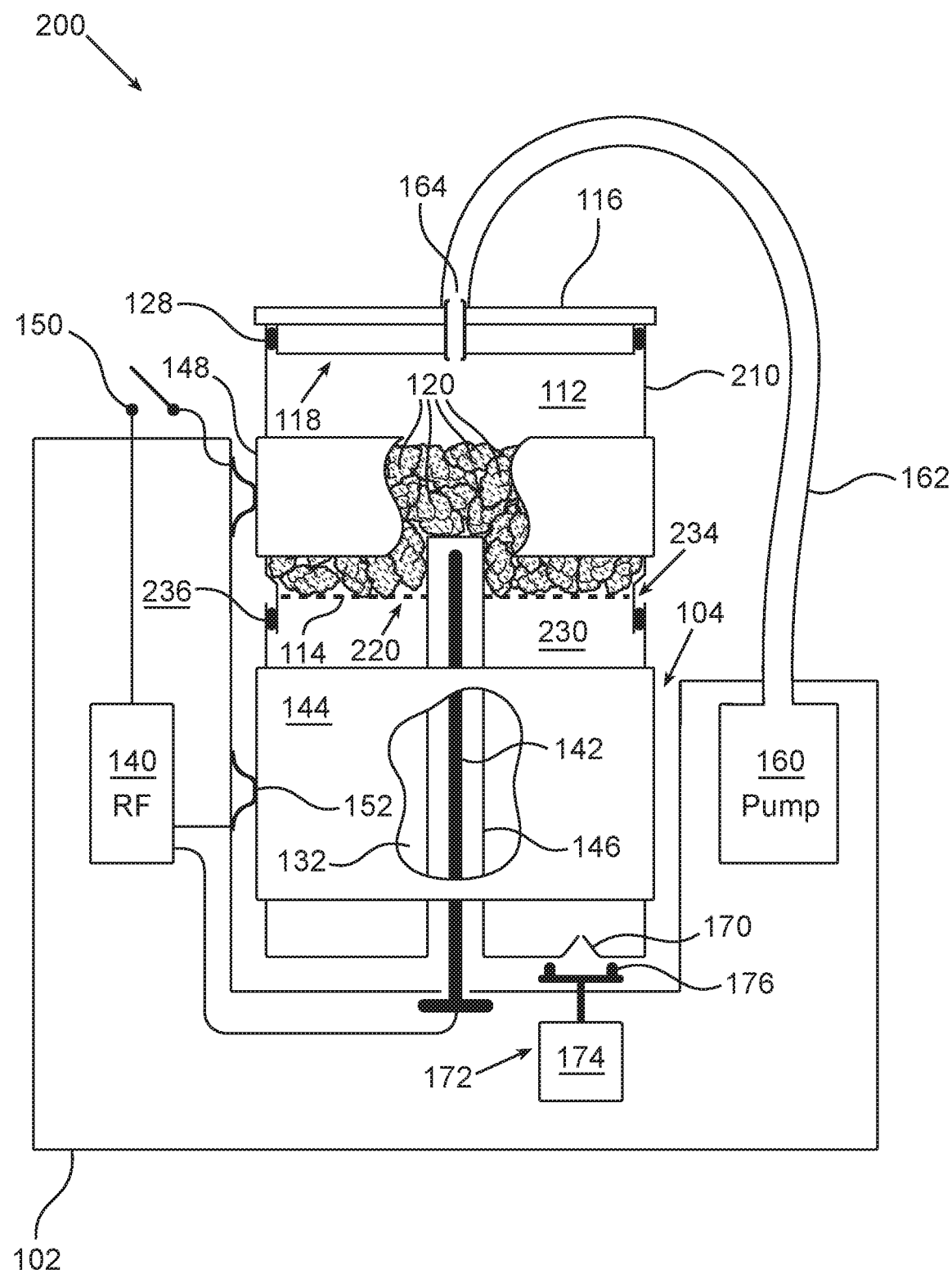
FIG. 2 schematically depicts an embodiment of a device for disinfecting herbs using plasma, in a sealable vessel which is detachable from a bottom vessel, the bottom vessel comprising a plasma generation region.

FIG. 2 schematically depicts an embodiment of a device 200 for disinfecting herbs according to an aspect of the invention. Device 200 is different from device 100 in that device 200 comprises a sealable vessel 210 which is detachable from a bottom vessel 230, bottom vessel comprising plasma generation region 132. Sealable vessel 210 comprises the treatment region 112, defined between net 114 and top cover 116, whereas net 114 extends along a bottom opening 220 of sealable vessel 210.

Bottom vessel 230 may be configured as a chamber with an opening 234 configured to sealingly connect to bottom opening 220 of sealable vessel 210, thereby providing fluid communication between the internal volumes of the two vessels. The sealed connection between bottom vessel 230 and sealable vessel 210 may be provided using an inter vessel seal 236 (a sealed connection herein means a leakless connection).

The exemplary embodiment depicted in FIG. 2 comprises electrode 142, cylindrical electrode 144 and additional cylindrical electrode 148 which is optional, as described above regarding device 100. Furthermore, the various possibilities and options described for electrodes configurations and methods of plasma generation in device 100, apply, mutatis mutandis, for device 200 as well.

Figure 3A:
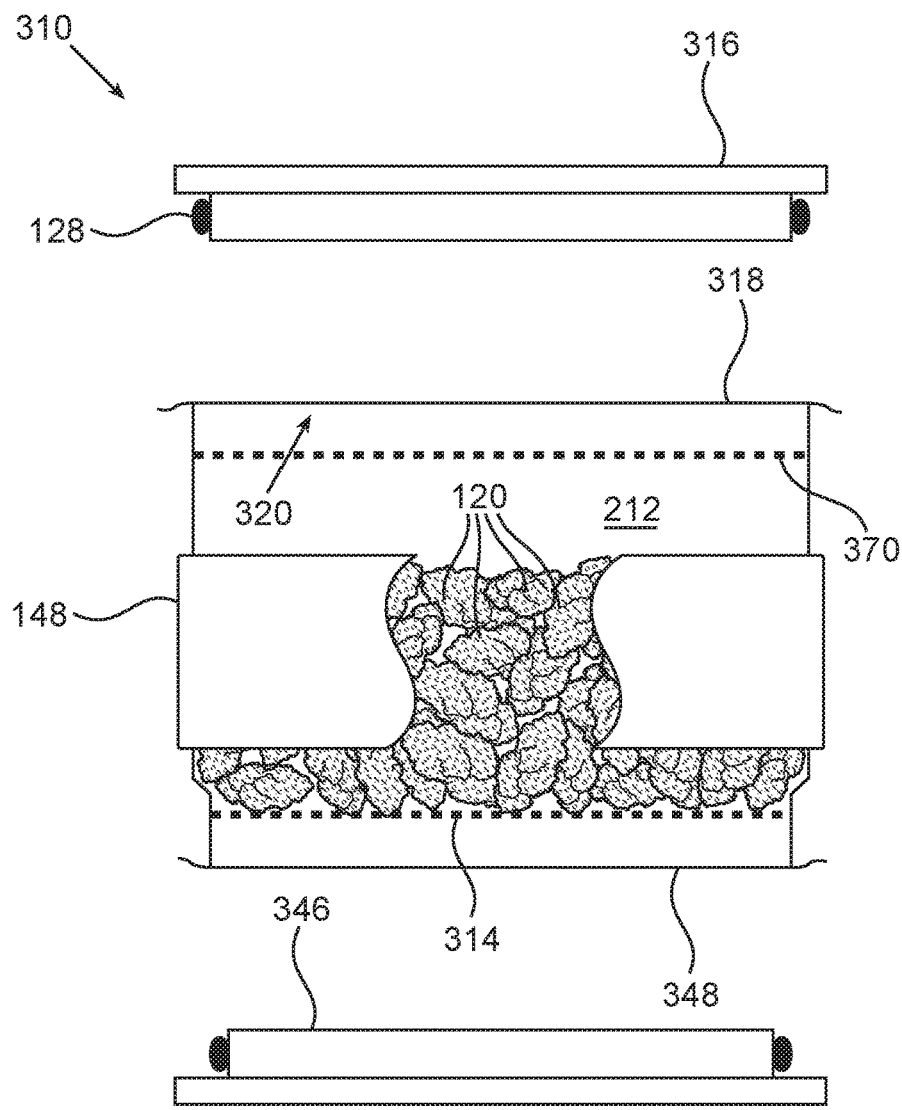
FIG. 3A schematically depicts an embodiment of a portable sealable vessel, configured for storing and transporting herbs and for enabling disinfecting herbs in the device of FIG. 2.

FIG. 3A schematically depicts an embodiment of a portable sealable vessel 310 according to an aspect of the invention. Portable sealable vessel 310 may be used to package herbs thereinside, e.g. by a manufacturer or a distributor, to store the herbs, ship or transport the herbs, and without removing the herbs from the portable sealable vessel, to provide plasma treatment to the herbs according to the teachings herein, to disinfect the herbs.

Portable sealable vessel 310 is different from sealable vessel 210 in that portable sealable vessel 310 comprises a microbially sealing net 314 instead of net 114 in sealable vessel 210. "Microbially sealing" herein means that the microbially sealing net is penetrable to gas molecules but microbial organisms may not penetrate therethrough. Microbial organisms may include viruses and prokaryotic and eukaryotic cells, including fungi and bacteria. Microbially sealing net 314 may be made as a filter having, for example, pores smaller than about 0.5 um, or smaller than about 0.2 um or even smaller than about 0.1 um. In some embodiments microbially sealing net 314 may be made from a commercial sterilization wrapping material which is penetrable to steam and gas but not penetrable to microbial organisms. According to some embodiments microbially sealing net 314 may be made from a Tyvek® (flashspun high-density polyethylene fibers) sheet.

Portable sealable vessel 310 may optionally further include a sealing top cover 316 and/or a top seal 318, configured to seal a top opening 320 of portable sealable vessel 310. Top seal 318 may be configured as a single-use sealing sheet, such as, e.g., an aluminized polymer sheet, sealingly glued or attached across the top opening 320. Additionally or alternatively sealing top cover 316 may be configured as a multi-use cover, adapted to allow repeated opening and closing of portable sealable vessel 310. Likewise, portable sealable vessel 310 may optionally be equipped with a bottom cover 346 and/or a bottom seal 348, configured to seal a bottom opening 350 of portable sealable vessel 310. Bottom cover 346 and bottom seal 348 are configured similarly to sealing top cover 316 and top seal 318, respectively.

Figure 3B:
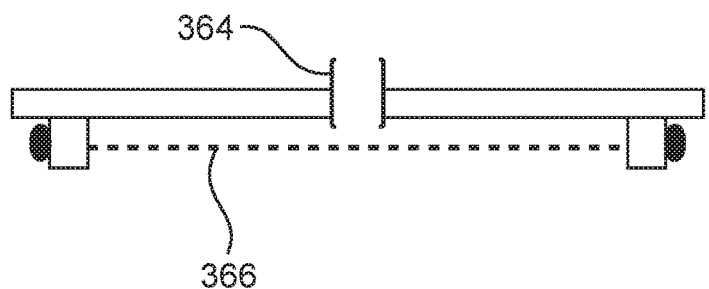
FIG. 3B schematically depicts an embodiment of a filtering cover configured for covering an opening of the portable sealable vessel of FIG. 3A during plasma disinfection in the device of FIG. 2.

According to some embodiments portable sealable vessel 310 may be equipped with a filtering cover 356 as schematically depicted in FIG. 3B, instead of sealing top cover 316. Filtering cover 356 comprises a filtered port 364 configured to connect to pump 160 via tube 162 (Shown in FIG. 1 and FIG. 2) to allow pumping of portable sealable vessel 310 during plasma excitation. Filtering cover 356 is different from sealing cover 114 in that filtered port 364 provides microbial sealing to portable sealable vessel 310 when tube 162 is disconnected from the port. In other words, filtered port 364 may comprise a microbial seal 366 that allows pumping therethrough but prevents penetration of microbes into portable sealable vessel 310 when the port is exposed to ambient air. According to some embodiments, the filtered port comprises a unidirectional valve that serves as a microbial seal.

Optionally, portable sealable vessel 310 may comprise a top microbially sealing net 370 which may, in some embodiments, be functionally identical to microbially sealing net 314. In such cases, when portable sealable vessel 310 comprises top microbially sealing net 370, filtering in the top cover may be redundant and sealing top cover 316 may be used instead of filtering top cover 356.

Thus, portable sealable vessel 310 may be provided to a customer or a consumer (herein a user) with herbs 120 microbially sealed inside, and optionally being completely sealed by single-use seals 318 and 348, and/or by multi-use covers 316 and 346 such seals or covers, as the case may be, defining a treatment region 212 therebetween For disinfecting the herbs by plasma, the user may remove the covers 316 and 346 and seals 318 and 348, and position the portable sealable vessel 310 in a plasma excitation device such as device 102. In the device, portable sealable vessel 310 may be sealingly connected to bottom vessel 230 (instead of sealable vessel 210) and covered with cover 116 for allowing proper plasma generation thereinside, as explained above for sealable vessel 110. Following plasma generation and disinfecting the herbs, top microbially sealing net 370 may be removed (e.g. by tearing the net and disposing of the remains) and herbs may be removed, partially or completely, from the portable sealable vessel. If some of the herbs are not consumed immediately following plasma disinfection, such herbs may be maintained inside the portable sealable vessel, and the vessel may optionally be closed and sealed by covers 316 and 346.

Alternatively or additionally, herbs may be packaged in portable sealable vessels 310 by a manufacturer, and transported to a supplier, whereas the supplier may perform disinfection to the herbs inside the portable sealable vessel prior to a sale to an end consumer. According to this method the consumer may be provided or delivered with an amount of herbs suitable for personal use, being stored in the original package pre-packaged by the manufacturer, and properly disinfected just prior to the delivery event.

Figure 4:
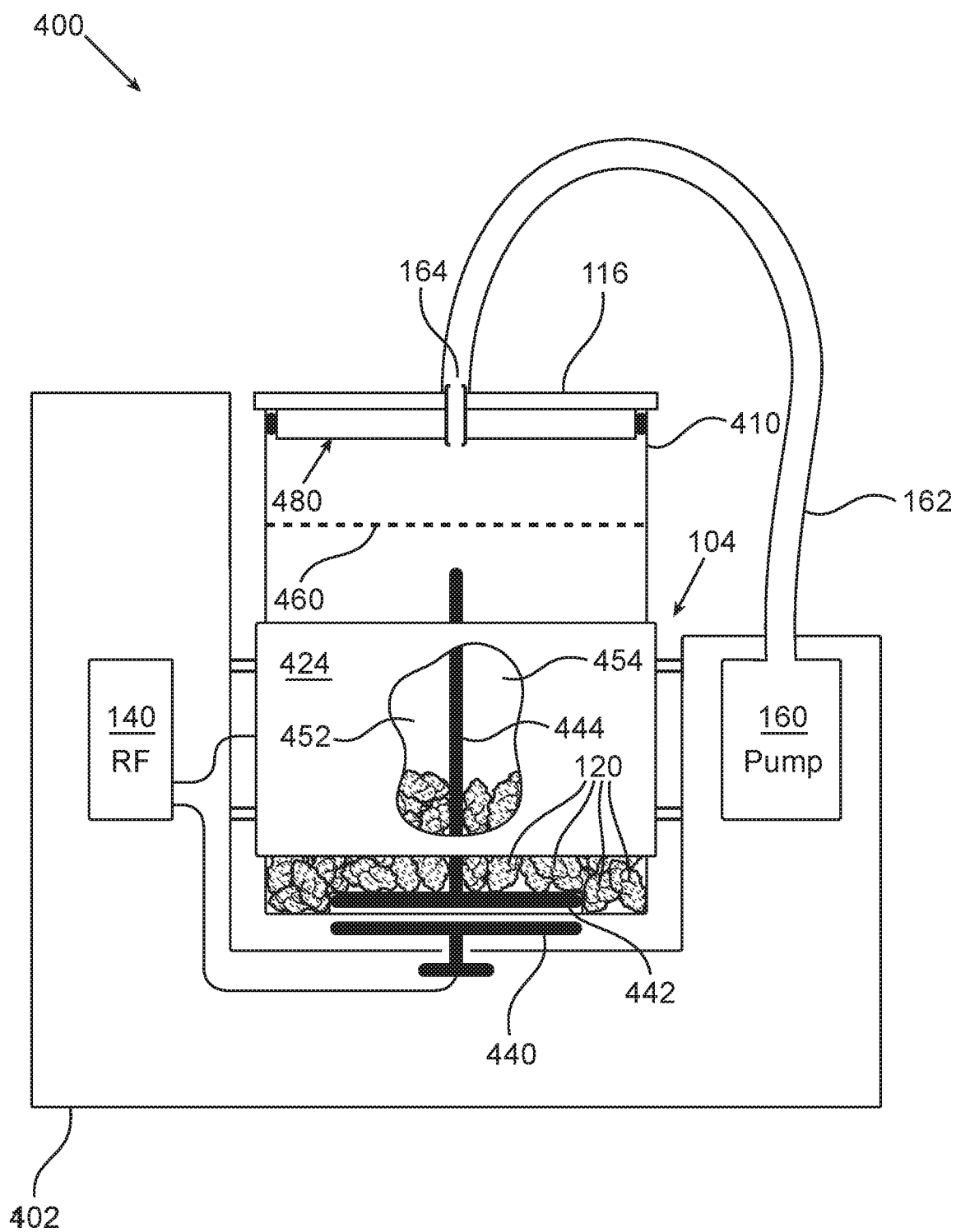
FIG. 4 schematically depicts an embodiment of a device and a portable sealable vessel, for disinfecting herbs using plasma, according to an aspect of the invention.

FIG. 4 schematically depicts an embodiment of a device 400 comprising a plasma excitation device 402 and a portable sealable vessel 410 according to an aspect of the invention. Portable sealable vessel 410 may be shaped as a container and configured to contain, store and transport a small amount of herbs intended for home or personal use as described above. Portable sealable vessel 410 may be made from a dielectric material and allow applying plasma thereinside to disinfect the herbs according to the teachings herein.

Plasma excitation device 402 is different from plasma excitation device 102 in that device 402 lacks valve 172 and switch 150. Further, plasma excitation device 402 comprises a cylindrical electrode 424 positioned in slot 104 and electrically associated with power source 140. Furthermore, plasma excitation device 402 comprises a plate 440 in slot 104 electrically associated—possibly electrically connected—with power supply 140. Plate 440 is dimensioned and configured to capacitively couple with a corresponding vessel plate 442 of portable sealable vessel 410, when portable sealable vessel 410 is positioned in slot 104, so as to induce a plasma generating EM field inside the vessel. Portable sealable vessel 410 comprises a rod electrode 444 electrically associated—possibly electrically connected—with vessel plate 442. Thus, when power source 140 is activated and provides RF power to the electrodes, a plasma generating electromagnetic field may be generated in a plasma generating region 452, which in this case overlaps with a treatment region 454, between the electrodes.

Portable sealable vessel 410 may optionally comprise a microbial seal 460 extending between the walls of the portable sealable vessel for microbially sealing a treatment region 450 defined below the microbial seal, from a top opening 480 of the vessel and the ambient. According to some embodiments, portable sealable vessel 410 may be packaged by the manufacturer with the herbs inside and shipped and/or transported being sealed by microbial seal 460. According to some embodiments, portable sealable vessel 410 may be further sealed during storage and shipment by a top cover such as e.g. sealing top cover 316. For plasma generation, the sealing top cover may be removed and replaced by top cover 116, and portable sealable vessel 410 may be positioned in slot 104 so that the treatment region is surrounded by cylindrical electrode 424, and electrode 444 is capacitively coupled with the power source.

For removing the herbs from the treatment region, the microbial seal 460 may be torn and disposed of enabling access to the treated herbs.

According to some embodiments the portable sealable vessel may comprise a central rod electrode that penetrates through the floor of the vessel, so that the rod electrode is in electrical contact (rather than being capacitively coupled) with the power source. According to some embodiments the floor of the portable sealable vessel, in any of the aforementioned embodiments, may be or may comprise a microbially sealing net such as microbial seal 460.

Figure 5:
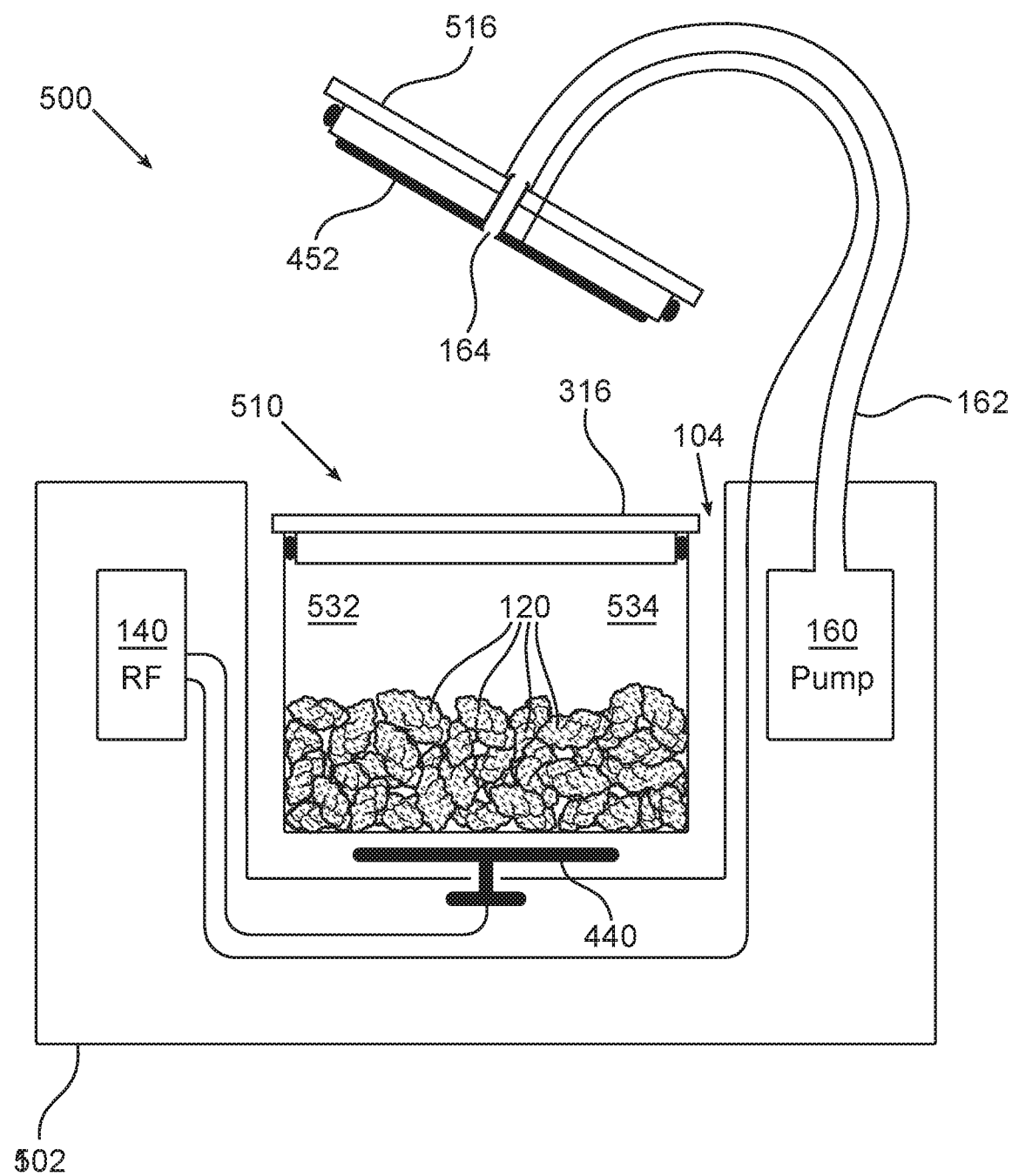
FIG. 5 schematically depicts an embodiment of a device and a portable sealable vessel lacking an electrode, for disinfecting herbs using plasma, and FIG. 6 schematically depicts an embodiment of a multi-slot device for disinfecting herbs using plasma in a multitude of sealable vessels simultaneously.

FIG. 5 schematically depicts an embodiment of a device 500 comprising a plasma excitation device 502 and a portable sealable vessel 510 according to an aspect of the invention. Portable sealable vessel 510 may be shaped as a container and configured to contain, store and transport a small amount of herbs intended for home or personal use as described above. Portable sealable vessel 510 may be made from a dielectric material and allow applying plasma thereinside to disinfect the herbs according to the teachings herein.

Portable sealable vessel 510 is different from portable sealable vessel 410 in that portable sealable vessel 510 lacks an electrode and/or an electric conductor. In other words, portable sealable vessel 510 is configured to enable plasma generation thereinside solely by electrodes comprised by plasma excitation device 502. According to some embodiments, portable sealable vessel 510 may be stored and transported with a sealing cover such as sealing cover 316. For plasma generation inside the vessel, the sealing cover may be replaced with an electrode cover 516 as schematically depicted in FIG. 5, Plasma excitation device 502 is different from plasma excitation device 402 in that device 502 is capable of activating plasma inside a portable sealable vessel which for itself lacks any electrode. In the exemplary embodiment depicted in FIG. 5, plate electrode 440 is positioned at the bottom of slot 104, beneath portable sealable vessel 510 (when portable sealable vessel 510 is positioned in the slot). A cover plate electrode 542 is attached to electrode cover 516, preferably on an inner surface thereof, being electrically associated (possibly electrically connected) to RF power source 140. When portable sealable vessel 510 is placed in the slot and sealing cover 316 is replaced by electrode cover 516, pump 160 may be used to evacuate the internal volume of the vessel. Activating the power source may apply a plasma generating EM field in a plasma generating region 532, which in this case overlaps with a treatment region 534, between plate electrode 440 and cover electrode 542, in a DBD mode. It should be understood that other electrodes configurations may be used, e.g. two or more cylindrical electrodes, or, alternatively, one or more helix, wound on the inner surface of slot 014, thereby being wound around portable sealable vessel 510. According to some embodiments portable sealable vessel 510 may be shaped differently from a cylinder, e.g. as a rectangular cuboid (a box). According to some embodiments a plasma generating EM field may be generated between two vertical plate electrodes arranged on opposite sides of the vessel.

According to some embodiments, gas may be forced—by a pressure pump or from a pressurized gas reservoir) not shown here)—into the sealable vessel. According to some embodiments gas may be forced through a gas port (not shown here), e.g. in the top cover of the vessel or in the bottom cover (if the vessel incorporates a bottom cover) or through a gas port on the vessel's body. According to some embodiments gas from the sealable vessel may leak outside through a leak aperture (e.g. as depicted in FIGS. 1 and 2), thus maintaining the pressure inside the vessel at about atmospheric pressure. According to some embodiments gas may be forced into the vessel through an inlet gas port, while the vessel is being pumped (e.g. as described in FIGS. 1-5) through an outlet gas port, thus allowing the forced gas to flush the vessel while possibly maintaining inside the vessel a pressure lower than atmospheric pressure. According to some embodiments the gas forced into the vessel may be an inert gas such as, for example, N2, helium or argon.

According to some embodiments, any of the devices depicted in FIGS. 1-5 may be further equipped with a validating sensor configured to sense actual plasma generation in the sealable vessel, thereby validating the disinfection process. According to some embodiments such a validating sensor may comprise an optical sensor, optically coupled, directly or via an optical coupling device such as for example an optical fiber, with the plasma generation region inside the sealable vessel. According to some such embodiments an optical fiber may be used to optically couple the optical sensor and the plasma generation region. The optical fiber may have one end configured to collect light from the plasma generation region whereas another end thereof may be optically associated with the optical sensor. The optical sensor may be electrically associated with a main controller of the device, and the controller may thus receive from the sensor a signal indicating whether or not the plasma generation region glows—indicating gas ionization—during supposed plasma generation.

Figure 6:
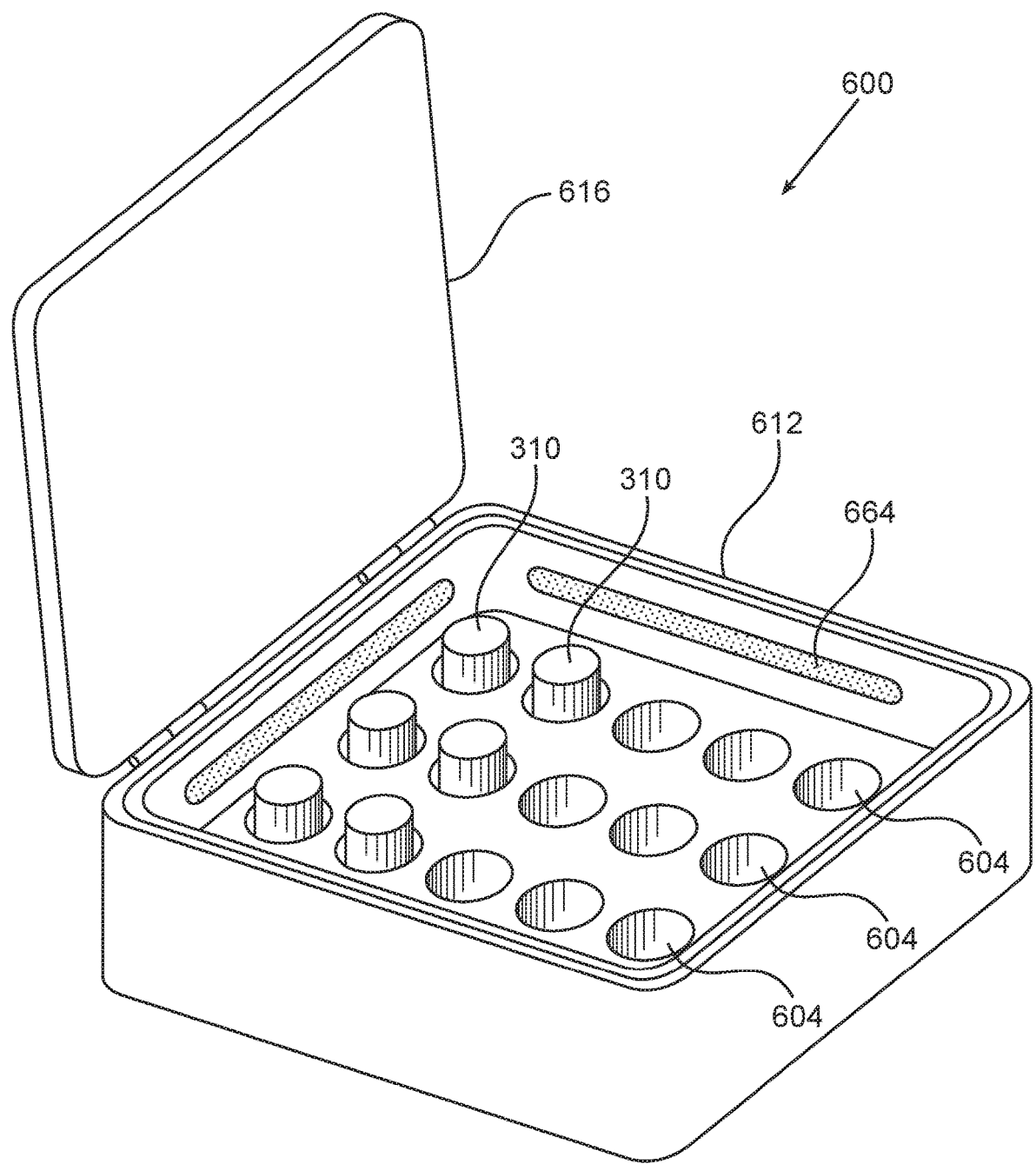

According to an aspect of the invention a multi-slots device is provided for disinfecting herbs in a multitude of sealed vessels in parallel (i.e. simultaneously). The multi slots device has a multitude of slots adapted to respectively receive a multitude of sealable vessels—e.g. sealable vessels as depicted in FIGS. 1-5—one in each slot. According to some embodiments the multitude of sealable vessels may be pumped by a single central vacuum pump. FIG. 6 schematically depicts an embodiment of a multi-slot device 600 comprising a multitude of slots 604 with a few of the slots occupying sealable vessels such as for example portable sealable vessel 310. The slots are arranged in a chamber 612 configured to be covered and sealed with a sealable cover 616. The chamber may further be pumped—through a pumping port 664 fluidly associated with a vacuum pump (not shown here). When the chamber is evacuated, the interiors of the sealable vessels are correspondingly evacuated also via respective gas ports or microbial seals or unidirectional valves of the respective vessels.

Alternatively or additionally, according to some embodiments an individual pump may be associated with each slot so as to exclusively pump a single vessel. Likewise, a central gas supply or individual gas supplies may be employed in some embodiments to force gas into the multitude of vessels, as described above. According to some embodiments the multi slots device may comprise a multitude of low-power power sources, each power source being exclusively associated with one slot to generated plasma in a single sealable vessel in the slot. According to some embodiments the multi slots device may comprise a single high-power power source configured to provide sufficient power to activate plasma in the vessels in all of the slots of the device. According to some embodiments an RF power splitter may be used to properly couple the high-power power source with the multitude of the slots (and the respective multitude of electrodes), so as to diminish or at least to minimize the effects of load variations in one slot on power delivery to other slots. When there are lass sealable vessels requiring plasma treatment than slots in the multi slots device, dummy vessels may be placed in the remaining (empty) slots. Additionally or alternatively, a vessel indicator (e.g. a micro switch) in each slot may be used to indicate whether or not a sealable vessel is placed in the respective slot. All the vessel indicators may be electrically associated with the controller and the controller may accordingly activate pumping and power supply only to those slots occupying sealable vessels.

Disinfection of *Cannabis* herbs was carried out successfully using the device of FIG. 1, and the results are summarized in Table 1. *Cannabis* flowers were grinded to form chunks and particles of typical sizes up to about 1 mm. 5 samples of 0.8 gr each of the grinded material were used for the experiment, of which three samples where disinfected according to the principles described above, and two samples were not disinfected, thus being used as reference. Disinfection was measured for both bacteria and fungi (mold).

| Sample | Weight [g] | Treatment time [min] | Final total count [CFU] | Total count Log reduction | Percent reduction [%] | Final mold count [CFU] | Mold count Log reduction | Percent reduction [%] |
|---|---|---|---|---|---|---|---|---|
| 1 | 0.8 | 5 | 3.60E+03 | 1.65 | 97.75 | 4.50E+03 | 1.18 | 93.38 |
| 2 | 0.8 | 5 | 6.30E+03 | 1.40 | 96.06 | 4.00E+03 | 1.23 | 94.12 |
| 3 | 0.8 | 9 | 1.10E+03 | 2.16 | 99.31 | 1.60E+02 | 2.63 | 99.76 |
| 4 | 0.8 | Reference | 1.50E+05 | | | 7.00E+04 | | |
| 5 | 0.8 | Reference | 1.70E+05 | | | 6.60E+04 | | |

Samples 1-3, each occupying a volume of about 2-3 cubic cm, were individually plasma treated in the direct scheme described above, in a vessel the size of an ordinary cup. Plasma operating parameters included a pressure of about 15 mbar and plasma generation at a duty cycle of about 30%. Plasma generation time was 5 minutes for samples 1 and 2, and 9 minutes for sample 3.

Bacteria count (Colony Forming Unit, CFU) for the two reference samples 4 and 5 were $1.5*10^5$ and $1.7*10^5$, respectively, with an average of $1.6*10^5$. Bacteria count for samples 1 and 2 were $3.6*10^3$ and $6.3*10^3$, with percent reduction of 97.7% and 96% respectively. Bacteria count for sample 3 (following a 9 minutes treatment) was $1.1*10^3$, with percent reduction of more than 99%. Further, mold count for the two reference samples 4 and were $7*10^4$ and $6.6*10^4$, respectively, with an average of $6.8*10^4$. Mold count for samples 1 and 2 were $4.5*10^3$ and $4.0*10^3$, with percent reduction of about 93%% and 94% respectively. Mold count for sample 3 was $1.6*10^2$, with percent reduction of more than 99.7%. Thus, the treatment succeeded in diminishing both the bacteria count and the mold count from disallowed levels to allowed levels (below $10^5$ CFU and $10^4$ CFU, respectively), in both the 5 minutes treatment duration and the 9 minutes duration.

It is thus concluded that disinfection of herbs from bacteria and/or mold, at reduction rates in the range of 80%-100% may be obtained by plasma treating according to the teachings herein. According to some embodiments reduction rates may be between 90%-100%; according to some embodiments reduction rates may be between 95% and 100%; according to some embodiments reduction rates may be between 99% and 100%.

There is thus provided according to an aspect of the invention a device (100, 200, 400, 500) for disinfecting herbs (120) using plasma. The device comprises a plasma excitation device (102, 202, 402, 502, 600) comprising a power source (140) configured to generate RF electromagnetic (EM) power, and a slot (104, 604) dimensioned to receive therein a sealable vessel. The device further comprises a sealable vessel (110, 210, 310, 410, 510) detachable from the plasma excitation device, dimensioned and configured to contain herbs in a treatment region (112, 212, 454, 534) of the sealable vessel and to be received in the slot of the plasma excitation device, the sealable vessel comprising an opening (118, 320, 480) allowing to add herbs into the sealable vessel and to remove herbs therefrom, and a cover (116, 316, 346, 356, 516) configured to sealingly close the opening. The device further comprises at least one electrode (142, 144, 148, 444, 424), positioned and configured so as to—when the sealable vessel is received in the slot—electrically associate with the power source, and, upon receiving from the power source a suitable RF EM power, to apply a plasma-generating EM field for producing cold plasma in a plasma generation region (132, 452, 532) of the sealable vessel, the plasma generation region having fluid connectivity with the treatment region.

According to some embodiments the electrode may be for example: a central electrode (142, 444) in the from of an elongated rod positioned in between walls of the sealable vessel; a cylindrical electrode (144, 148, 424) surrounding at least a portion of the sealable vessel, a helix wound around at least a portion of the sealable vessel, a plate (440, 452), and a piezoelectric element operable as a high voltage transformer.

According to some embodiments the sealable vessel contains no more than about 300 cc. According to some embodiments the plasma generation region is distant from the treatment region by no more than about 7 cm. According to some embodiments the power source produces no more than about 10 W.

According to some embodiments the sealable vessel comprises a net (114, 314) permeable to gas and configured to prevent the herbs from penetrating therethrough. The net may be positioned in the sealable vessel so as to section the interior of the vessel to the treatment region defined between the net, the walls of the sealable vessel and the opening, and to a remaining portion (130, 230). The remaining portion may overlap, at least partially, with the plasma generating region. According to some embodiments the net is configured as a pot. According to some embodiments the at least one electrode comprises the net. According to some embodiments the net is removable from the sealable device.

According to some embodiments the plasma excitation device further comprises a gas pump (160) fluidly and detachably associated with the sealable vessel, and configured to reduce the pressure in the sealable vessel. The pressure in the sealable vessel during plasma activation may be below about 0.5 Atm, for example 0.2 Atm or 0.1 Atm or 0.05 Atm or 0.02 Atm or even about 0.01 Atm or even less. According to some embodiments the device comprises a valve (172) configured to open or shut a controlled leakage aperture (170) of the sealable vessel. The leakage aperture is configured to allow, when open, leakage of air into the sealable vessel so as to promote displacement of gas inside the sealable vessel during pumping.

According to some embodiments the at least one electrode (144, 148, 444) is comprised by the sealable vessel. According to some embodiments the at least one electrode (142, 440, 452) is comprised by the plasma activation device.

There is further provided according to an aspect of the invention a sealable vessel (110, 210, 310, 410, 510) for containing herbs during disinfection by plasma treatment. The sealable vessel comprises an opening (118, 320, 480) allowing to add herbs into the sealable vessel and to remove herbs therefrom. The sealable vessel further comprises a net (114, 314) permeable to gas and configured to prevent penetration of herbs therethrough. The net is positioned in the sealable vessel so as to section the interior of the vessel to a treatment region (112, 212, 454, 534) defined between the net, the walls of the sealable vessel and the opening, and to a remaining portion (130, 230). The treatment region is configured to receive herbs thereinside. The sealable vessel further comprises a plasma generation region (132, 452, 532) overlapping at least partially with the remaining portion. The sealable vessel further comprises a removable cover (116, 316, 346, 356, 516) configured to sealingly close the opening. In some embodiments plasma may be generated within the treatment region, for example in sealable vessel 110, sealable vessel 210 and sealable vessel 310 when cylindrical electrode 148 is in use.

According to some embodiments the cover comprises a gas port (164, 364) configured to fluidly connect to a tube and allowing to pump gas from the interior of the portable sealable vessel or to insert gas thereto. According to some embodiments the gas port comprises a microbial filter (366) configured to allow pumping therethrough and to prevent penetration of microorganisms therethrough.

According to some embodiments the portable sealable vessel further comprises at least one electrode. The electrode may be for example: a central electrode (444) shaped as an elongated rod, arranged inside the plasma generation region, a cylindrical electrode (144, 148) enveloping at least a portion of the plasma generation region, a helix wound around at least a portion of the plasma generation region, a plate and a piezoelectric element configured as a high voltage transformer having its high voltage end inside the plasma generation region. According to some embodiments the net is electrically conducting and is used as an electrode. According to some embodiments the at least one electrode is configured to be electrically contacted (144, 148) or electrically coupled, capacitively (444) or inductively, from outside of the vessel.

According to some embodiments the opening (118, 320, 480) is sealed with a single-use seal (318, 348, 370, 460). According to some embodiments the opening (118, 320, 480) is sealed with a microbial seal (460, 370, 314).

According to some embodiments the sealable vessel further comprises a leakage aperture (170) configured to allow leakage of air into the sealable vessel so as to promote displacement of gas inside the sealable vessel, when the vessel is pumped via the gas port. According to some embodiments the gas port (364) comprises a unidirectional valve allowing gas flow out of the sealable vessel. According to some embodiments the sealable vessel comprises a portable sealable vessel (210, 310) comprising the treatment region (112, 212), the portable sealable vessel being sealingly detachable from the remaining portion (230).

There is further provided according to an aspect of the invention a multi-slot device (600) for disinfecting herbs by plasma treatment. The multi-slot device comprises a chamber 612, sealable with a cover 616. The multi-slot device further comprises a multitude of slots 604 arranged in the chamber and configured to receive, respectively, a multitude of sealable vessels (110, 210, 310, 410, 510), a single sealable vessel in a single slot. The multi-slot device further comprises a vacuum pump fluidly associated with the chamber and configured to evacuate the chamber and reduce the air pressure there inside to below 0.5 Atm. The multi-slot device further comprises at least one power source configured to produce a RF EM power. The multi-slot device further comprises a multitude of electrodes (142, 144, 148, 444, 424) electrically associated with the at least one power source and respectively associated with the multitude of sealable vessels in the slots, thereby being configured to provide, upon receiving a RF EM power, a plasma generating EM field in the interior of the multitude of sealable vessel which are arranged in the multitude of slots.

According to some embodiments the at least one power source is electrically associated with the multitude of electrodes via a power splitter, thereby being configured to supply EM power for plasma generating EM fields in a multitude of sealable vessels. According to some embodiments the at least one power source comprises a multitude of power sources 140, each being electrically respectively associated with the multitude of electrodes of the multitude of sealable vessels.

It is appreciated that certain features of the invention which are described in the context of separate embodiments, may also be provided in combination in a single embodiment. Conversely, various features of the invention, which are described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A device for disinfecting herbs using plasma, the device comprising:
   a plasma excitation device including a power source configured to generate radio frequency (RF) electromagnetic (EM) power, and a slot dimensioned to receive therein a sealable vessel;
   a sealable vessel detachable from the plasma excitation device, dimensioned and configured to contain herbs in a treatment region of the sealable vessel and to be received in the slot of the plasma excitation device, the sealable vessel including an opening allowing to add herbs into the sealable vessel and to remove herbs therefrom, and a cover configured to sealingly close the opening, and further including a net permeable to gas and configured to prevent the herbs from penetrating therethrough, positioned in the sealable vessel so as to sect the interior of the vessel to said treatment region defined between the net, the walls of the sealable vessel and the opening, and to a remaining portion, at least partially overlapping with a plasma generation region, and
   at least one electrode, positioned and configured so as to—when the sealable vessel is received in the slot—electrically associate with the power source, and, upon receiving from the power source a suitable RF EM power, to apply a plasma-generating EM field for producing cold plasma in the plasma generation region of the sealable vessel, the plasma generation region having fluid connectivity with the treatment region.

2. The device of claim 1 wherein the at least one electrode includes at least one of: a central electrode in the form of an elongated rod positioned in between walls of the sealable vessel; a cylindrical electrode surrounding at least a portion of the sealable vessel; a helix; or a piezoelectric element operable as a high voltage transformer.

3. The device of claim 1 wherein the sealable vessel contains no more than about 300 cc, the plasma generation region is distant from the treatment region by no more than about 7 cm and the power source produces no more than about 10 W.

4. The device of claim 1 wherein the at least one electrode includes the net.

5. The device of claim 1 wherein the net is removable from the sealable vessel.

6. The device of claim 1 wherein the plasma excitation device further includes a gas pump fluidly and detachably associated with the sealable vessel, and configured to reduce the pressure in the sealable vessel.

7. The device of claim 6, further comprising a valve configured to open or shut a controlled leakage aperture of the sealable vessel, the controlled leakage aperture being configured to allow, when open, leakage of air into the sealable vessel so as to promote displacement of gas inside the sealable vessel during pumping.

8. The device of claim 1 wherein the sealable vessel includes the at least one electrode.

* * * * *